US006598596B2

(12) United States Patent
Wachsman et al.

(10) Patent No.: US 6,598,596 B2
(45) Date of Patent: Jul. 29, 2003

(54) SOLID STATE POTENTIOMETRIC GASEOUS OXIDE SENSOR

(75) Inventors: Eric D. Wachsman, Gainesville, FL (US); Abdul Majeed Azad, Columbus, OH (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/966,240

(22) Filed: Sep. 28, 2001

(65) Prior Publication Data

US 2003/0066519 A1 Apr. 10, 2003

(51) Int. Cl.[7] .................. F02D 41/14; G01N 27/407
(52) U.S. Cl. .................. 123/703; 204/426; 204/429; 205/781
(58) Field of Search ............... 123/703; 204/421–429; 205/781, 784

(56) References Cited

U.S. PATENT DOCUMENTS

| | | | |
|---|---|---|---|
| 4,005,001 A | 1/1977 | Pebler | 204/426 |
| 4,770,760 A | 9/1988 | Noda et al. | 204/425 |
| 4,927,517 A | 5/1990 | Mizutani et al. | 204/406 |
| 4,950,380 A | 8/1990 | Kurosawa et al. | 204/406 |
| 5,034,107 A | 7/1991 | Wang et al. | 205/781 |
| 5,034,112 A | 7/1991 | Murase et al. | 204/406 |
| 5,217,588 A | 6/1993 | Wang et al. | 205/781 |
| 5,397,442 A | 3/1995 | Wachsman | 205/781 |

FOREIGN PATENT DOCUMENTS

WO        WO 97/42495      * 11/1997      ......... G01N/27/407

OTHER PUBLICATIONS

Yamaura, et al., Selective CO Detection by Using Indium Oxide–Based Semiconductor Gas Sensor, J. Electrochem. Soc., vol. 143, No. 2, Feb. 1996, pp. L36–L37.
Fukui, et al., CO Gas Sensor Based on Au–$La_2O_3$ Loaded $SnO_2$ Ceramic, Sensors and Actuators B 24–25 (1995) pp. 486–490.
Miura, et al., Construction and Working Mechanism of Sulfur Dioxide Sensor Utilizing Stablized Zirconia and Metal Sulfate, J. Electrochem. Soc., vol. 143, No. 1, Feb. 1996, pp. 609–613.

* cited by examiner

Primary Examiner—Tony M. Argenbright
(74) Attorney, Agent, or Firm—Akerman Senterfitt

(57) ABSTRACT

A solid state electrochemical cell (10a) for measuring the concentration of a component of a gas mixture (12) includes first semiconductor electrode (14) and second semiconductor electrode (16) formed from first and second semiconductor materials, respectively. The materials are selected so as to undergo a change in resistivity upon contacting a gas component, such as CO or NO. An electrolyte (18) is provided in contact with the first and second semiconductor electrodes. A reference cell can be included in contact with the electrolyte. Preferably, a voltage response of the first semiconductor electrode is opposite in slope direction to that of the second semiconductor electrode to produce a voltage response equal to the sum of the absolute values of the control system uses measured pollutant concentrations to direct adjustment of engine combustion conditions.

65 Claims, 9 Drawing Sheets

| Cell | Electrodes | Slope (mV/decade CO) | T/°C |
|---|---|---|---|
| I | $TiO_2$/Au | -70.15 | 500 |
| | | -63.77 | 600 |
| | | -36.44 | 700 |
| II | TYPd5/Au | 85.17 | 500 |
| | | 69.60 | 600 |
| | | 25.75 | 650 |
| III | $TiO_2$/TYPd5 | -94.43 | 600 |
| | | -34.80 | 700 |
| IV | $ZnMoO_4$/Au | -47.06 | 400 |
| | | -70.32 | 450 |
| | | -58.91 | 500 |
| V | $WR_3$/Au | -108.59 | 550 |
| | | -126.43 | 600 |
| VI | $SnO_2$/$MoO_3$ | 53.973 | 450 |
| | | 89.57 | 500 |

SOLID STATE POTENTIOMETRIC GASEOUS OXIDE SENSOR

STATEMENT REGARDING FEDERALLY SPONSORED RESEARCH OR DEVELOPMENT

The United States Government has rights in this invention pursuant to Contrat No. NAG10-0274 between the National Aeronautics and Space Administration (NASA) and the University of Florida.

FIELD OF THE INVENTION

The invention relates generally to measurement of components in a gas stream, and more particularly to an electrochemical apparatus and method for measuring the concentration of gaseous oxides in a gas mixture.

BACKGROUND

Various devices and methods have been described for determining the concentration of oxides of nitrogen ($NO_x$, for example, $N_2O$, $NO$ and $NO_2$), oxides of carbon ($CO_x$ for example, $CO$ and $CO_2$), oxides of sulfur ($SO_x$ for example, $SO_2$ and $SO_3$), and other oxide compounds in a gas mixture. Such gases may include gaseous oxygen ($O_2$), nitrogen ($N_2$), other inert gases, as well as combustible gases such as $H_2$ and various hydrocarbons.

Most modern automobiles use an $O_2$ sensor which is disposed in the exhaust system together with an on board computer to control the amount of fuel injected for combustion. Usually, the computer only utilizes oxygen sensor data ("closed loop" mode) under cruise conditions to improve efficiency. The $O_2$ sensor outputs a voltage when the oxygen content of the exhaust gasses falls below the norm for the atmosphere. The voltage range is generally from 0 to 1 volt. The $O_2$ sensor is not sensitive to gases other than $O_2$.

Oxygen in the air is consumed when fuel burns. Accordingly, increasing the amount of fuel for a given amount of air (a richer mixture) will deplete a greater part of the available oxygen. The $O_2$ sensor in the exhaust pipe responds to this condition by raising the output voltage. Thus, the $O_2$ sensor can help to maximize gas mileage and minimize the emission of pollutants. However, a typical $O_2$ sensor has poor sensitivity in the range needed for acceleration, where the typical air/fuel ratio used in most cars is 12.5:1. Conventional $O_2$ sensors are also sensitive to heat. Meaningful sensor output results only when exhaust temperatures are between approximately 360° C. and approximately 900° C.

The presence and concentration of gaseous oxide compounds have been measured using electrochemical sensing devices and methods which can generally be classified as either oxygen pumping sensors or potentiometric sensors. For example, U.S. Pat. No. 4,005,001 to Pebler, U.S. Pat. No. 4,770,760 to Noda et al., U.S. Pat. No. 4,927,517 to Mizutani et al., U.S. Pat. No. 4,950,380 to Kurosawa et al., U.S. Pat. No. 5,034,107 to Wang et al., and U.S. Pat. No. 5,034,112 to Murase et al and U.S. Pat. No. 5,217,588 to Wang disclose sensors for identifying presence and concentration of gaseous oxide compounds. Oxygen pumping sensors are amperometric sensors which "pump" $O_2$ through the cell at a rate proportional to electrical current induced in the pumping cell. However, most of the sensors referenced above are potentiometric sensors. Potentiometric sensors operate without "pumping" and generate a voltage rather than an output current.

For example, Wang discloses a sensor formed from two electrochemical cells on a zirconia electrolyte. One cell senses only oxygen gas and the other cell senses all the gases which contain oxygen, including the oxygen gas. Both electrochemical cells are exposed to the same gas mixture, and the differences between the sensed signals is a measure of the concentration of $NO_x$ in the gas mixture.

Murase et al. discloses a sensor in which a catalyst for reducing $NO_x$ is placed on an electrolyte adjacent to a pumping cell. A current is induced in the pumping cell to control the oxygen concentration in the environment around the pumping cell. When the oxygen concentration is depleted to a predetermined level, the catalyst supposedly begins to deplete $NO_x$, and the oxygen concentration of $NO_x$ is determined by measuring the current supplied to the pumping cell.

While pumping type sensors can be used to pump $O_2$ from NO to form $N_2$ and $O_2$, they cannot generally be used to pump $O_2$ from CO since C is not a gas and will deposit as a solid. Regarding potentiometric sensors such as the sensor disclosed by Wang, these sensors do not provide accurate measurement of CO or other oxide compounds in gas mixtures, because the electrodes used for the electrochemical cells are not sufficiently selective with respect to oxygen and oxide compounds, such as CO and NO. Moreover, if the gas mixture contains a relatively low oxide concentration compared with that of oxygen, an accurate determination of the oxide concentration is difficult. In exhaust gases or emissions produced by internal combustion engines or furnaces, the concentration of oxygen is typically much higher than the CO concentration. Thus, it is difficult to accurately measure the CO concentration in these gas mixtures using the typical pumping cell.

Another type of sensor described in U.S. Pat. No. 5,397,442 to Wachsman seeks to obviate this problem by providing a sensor including a chamber designed to receive a gas mixture in which two electrochemical cells are situated. Each cell is comprised of an electrode housed inside the chamber and an electrode outside the chamber, in which the internal and external electrodes are separated by an oxygen ion-conducting solid electrolyte. The first electrochemical cell is designed to consume oxygen by electrochemical reduction without appreciably consuming $NO_x$, while the second electrochemical cell is relatively selective for the electrochemical reduction of $NO_x$. A potential difference is applied across the first cell so that oxygen is removed from the chamber and then an electrical characteristic (voltage, current, power, etc.) of the second cell is measured that corresponds to the concentration of the oxide in the gas mixture. However, this system is somewhat complex and, because entry of gas into the chamber is diffusion limited, the response time of the sensor can be relatively slow.

SUMMARY

A solid state electrochemical cell for measuring the concentration of a component of a gas mixture includes a first semiconductor electrode and a second semiconductor electrode, the electrodes comprising first and second semiconductor materials, respectively. The electrode materials are selected so as to undergo a change in resistivity upon contacting the component. A change in resistivity of the electrode materials results in a change in voltage across the electrochemical cell. An electrolyte is disposed in contact with the first and second semiconductor electrodes. The electrochemical cell can include a reference electrode in contact with the electrolyte.

At least one metal layer can be disposed on a portion of the semiconductor electrodes. The electrochemical cell can also include a detector for measuring an electrical characteristic generated by the electrochemical cell.

The semiconductor materials can include a metal oxide. The metal oxide is preferably $SnO_2$, $TiO_2$, $TYPd_5$, $MoO_3$, $ZnMoO_4$ or WR3, where $TYPd_5$ and $WR_3$ are acronyms defined below. The acronym $TYPd_5$ is used herein to represent a composite prepared by selecting $TiO_2$ (titania), $Y_2O_3$ (yttria) and Pd in a weight ratio of approximately 85:10:5. Anatase titania is mixed with yttria and Pd metal powder in the composition described above. The powder is then applied onto the solid electrolyte in a slurry, and then sintered at approximately 650° C. for 1 hr.

The acronym $WR_3$ will be used herein to represent a composite which can be formed from the decomposition of $Rh_2WO_6$ at temperatures above approximately 1130° C. into $WO_3$ and metallic Rh. Oxygen is liberated in the decomposition reaction leaving a mixture of $WO_3$ and 2Rh.

By selecting a first semiconductor material that exhibits a voltage response opposite in slope direction, the response being a function of detected gas concentration, to that of the second semiconductor material, the resulting voltage signal measured across the electrodes is substantially equal to the sum of the absolute values of individual voltage responses of the electrodes. The gas component measured can include CO.

The electrolyte is preferably an oxygen ion-conducting electrolyte. The oxygen ion-conducting electrolyte can be based on $ZrO_2$, $Bi_2O_3$ or $CeO_2$. Preferred oxygen ion-conducting electrolytes are electrolyte mixtures, the mixtures generally including a base material, such as $ZrO_2$, $Bi_2O_3$ or $CeO_2$ and one or more dopants, such as calcia (CaO) and yttria ($Y_2O_3$) which can function as stabilizers, or some other suitable oxygen ion-permeable material. For example, yttria stabilized zirconia (YSZ) electrolytes can be formed by mixing yttria and $ZrO_2$. Electrolytes that conduct ionic species other than oxygen ions, e.g., halides, are well known in the art and also find utility in the invention for measuring halogen-containing gas species.

A solid state electrochemical cell for measuring the concentration of a component of a gas mixture includes a first semiconductor electrode and a second semiconductor electrode, the electrodes comprising first and second semiconductor materials, respectively, the materials selected so as to undergo a change in resistivity upon contacting the component. The first semiconductor material is selected to exhibit a voltage response opposite in slope direction, the response being a function of detected gas concentration, to that of the second semiconductor material, whereby a voltage signal measured across the electrodes is substantially equal to the sum of the absolute values of individual voltage responses of the electrodes. An electrolyte is disposed in contact with the first and second semiconductor electrodes.

A solid state electrochemical apparatus for measuring the concentration of at least two components of a gas mixture includes a plurality of electrochemical cells, the electrochemical cells each formed by two semiconductor electrodes. The semiconductor electrodes are formed from semiconductor materials, the materials selected so as to undergo a change in resistivity upon contacting at least one of the components in the gas mixture. An electrolyte is disposed in contact with the first and second semiconductor electrodes. At least one metal layer can be disposed on a portion of the semiconductor electrodes. The electrochemical apparatus can include a detector for measuring an electrical characteristic generated by the electrochemical cell.

At least one of the semiconductor materials can include a metal oxide, such as $La_2CuO_4$, $SnO_2$, $TiO_2$, $TYPd_5$, $MoO_3$, $ZnMoO_4$ or $WR_3$. At least one electrochemical cell can include a first electrode comprising a first semiconductor material having a voltage response opposite in slope direction, the response being a function of detected gas concentration, to that of the second semiconductor material, whereby a voltage signal measured across the first and second electrodes is substantially equal to the sum of the absolute values of individual voltage responses of the first and second semiconductor electrodes. The components measured can include CO and NO.

The electrolyte is preferably an oxygen ion-conducting electrolyte. The oxygen ion-conducting electrolyte can be based on $ZrO_2$, $Bi_2O_3$ or $CeO_2$. The electrochemical apparatus can include a reference electrode in contact with the electrolyte.

An electrochemical apparatus for measuring the concentration of a component of a gas mixture includes a plurality of electrochemical cells connected in series, the electrochemical cells each having a first electrode and a second electrode. At least one of the electrodes includes a material selected so as to undergo a change in resistivity upon contacting the component. An electrolyte is disposed in contact with the first and second electrodes. At least one of the electrodes in the plurality of electrochemical cells can include metal oxide semiconductor materials, such as $La_2CuO_4$, $SnO_2$, $TiO_2$, $TYPd_5$, $MoO_3$, $ZnMoO_4$ or $WR_3$. For CO detection, opposing electrodes in cells can both be metal oxide semiconductor materials, the metal oxide materials selected from $SnO_2$, $TiO_2$, $TYPd_5$, $MoO_3$, $ZnMoO_4$ or $WR_3$.

The electrochemical apparatus can include at least one metal layer disposed on a portion of the metal oxide-semiconductor materials. The electrochemical apparatus can include a detector for measuring an electrical characteristic generated by the electrochemical apparatus.

Preferably, cells having two semiconducting electrodes are formed from a first metal oxide semiconductor material which exhibits a voltage response being a function of detected gas concentration opposite in slope direction to the response of the second metal oxide semiconductor material, whereby a voltage signal measured across the electrodes is substantially equal to the sum of the absolute values of individual voltage responses of the electrodes. The measured component can include CO and NO.

The electrolyte is preferably an oxygen ion-conducting electrolyte, such as electrolytes based on $ZrO_2$, $Bi_2O_3$ and $CeO_2$. The electrochemical apparatus can include a reference electrode in contact with the electrolyte.

A solid state electrochemical cell for measuring the concentration of CO in a gas mixture includes a first semiconductor electrode, the first semiconductor electrode including a first semiconductor material selected so as to undergo a change in resistivity upon contacting CO. The first semiconductor material can be $TiO_2$, $TYPd_5$, $MoO_3$, $ZnMoO_4$ or $WR_3$. A second electrode and an electrolyte is provided, the electrolyte in contact with the first and second electrodes.

The second electrode can preferably include a metal oxide semiconductor material such as $SnO_2$, $TiO_2$, $TYPd_5$, $MoO_3$, $ZnMoO_4$ or $WR_3$. At least one metal layer can be disposed on at least a potion of the semiconductor electrode materials. The electrochemical apparatus can include a detector for measuring an electrical characteristic generated by the electrochemical apparatus. A reference electrode can also be disposed in contact with the electrolyte.

A method for measuring the concentration of CO in a gas mixture includes the steps of exposing the gas mixture to a solid state electrochemical cell. The electrochemical cell is formed from (i) a semiconductor electrode, the semiconductor electrode comprising a semiconductor material, the semiconductor material selected so as to undergo a change in resistivity upon contacting CO, wherein the semiconductor material can include at least one selected from the group of materials consisting of $TiO_2$, $TYPd_5$, $MoO_3$, $ZnMoO_4$, $WR_3$; (ii) a second electrode, and (iii) an electrolyte in contact with the first and second electrodes. An electrical signal generated by the electrochemical cell is measured to determine. the concentration of the component. The second electrode can also be formed from a semiconductor electrode.

When two semiconducting electrodes are provided, the first semiconductor material can preferably be selected to exhibit a voltage response opposite in slope direction, the response being a function of detected gas concentration, to that of the second semiconductor material, whereby a voltage signal measured across the electrodes is substantially equal to the sum of the absolute values of individual voltage responses of the electrodes. At least one of the semiconductor materials can include a metal oxide. The metal oxide can be $SnO_2$, $TiO_2$, $TYPd_5l$ $MoO_3$, $ZnMoO_4$ or $WR_3$. The component measured can include CO.

A method for operating a combustion process, such as an engine, includes the steps of electrochemically determining the concentration of at least one exhaust pollutant emitted by the combustion process during operation, and adjusting combustion conditions based on concentrations of the exhaust pollutant determined in the determining step. The method can include the step providing an electrochemical cell, the electrochemical cell including (i) a first semiconductor electrode, (ii) a second semiconductor electrode, the electrodes comprising first and second semiconductor materials, respectively, the materials selected so as to undergo a change in resistivity upon contacting the pollutant, and (iii) an electrolyte in contact with the first and second semiconductor electrodes.

Rather than providing a single electrochemical cell, an electrochemical apparatus including a plurality of electrochemical cells can be provided. In one embodiment, the plurality of electrochemical cells can detect at least two of the exhaust pollutants, the plurality of electrochemical cells formed from first and second semiconductor electrodes, respectively, the electrode materials selected so as to undergo a change in resistivity upon contacting the pollutants. An electrolyte is provided in contact with the respective first and second semiconductor electrodes.

The method can include the step providing an electrochemical cell stack including a plurality of electrochemical cells connected in series, the electrochemical cells each including a first electrode and a second electrode. At least one of the electrodes is formed from a material selected so as to undergo a change in resistivity upon contacting the pollutant. An electrolyte is provided in contact with the first and second electrodes of respective electrochemical cells.

The method can include the step of providing an electrochemical cell, the electrochemical cell including (i) a semiconductor electrode, the semiconductor electrode comprising a semiconductor material selected so as to undergo a change in resistivity upon contacting CO, wherein the semiconductor material is $TiO_2$, $TYPd_5$, $MoO_3$, $ZnMoO_4$ or $WR_3$ and (ii) a second electrode. An (iii) electrolyte is provided in contact with the semiconductor electrode and the second electrode. The second electrode can be a semiconducting electrode.

Internal combustion engines, such as those included in motor vehicles, can utilize the invention. For example, an internal combustion engine can include an at least one cylinder, the cylinder for combusting a fuel mixture therein, the engine emitting a gas mixture comprising a plurality of pollutants. An electrochemical emission sensor is disposed to receive the emitted gas mixture and for determining the concentration of at least one of the plurality of pollutants. A feedback and control system is provided for receiving pollutant gas concentration data from the emission sensor and for directing adjustment of engine combustion conditions. The emission sensor can include an electrochemical cell, the electrochemical cell formed from a first semiconductor electrode and a second semiconductor electrode, the electrodes including first and second semiconductor materials, respectively. The electrode materials are selected so as to undergo a change in resistivity upon contacting the pollutants. An electrolyte is disposed in contact with the first and second semiconductor electrodes. Alternatively, the emission sensor can include an electrochemical apparatus, the electrochemical apparatus including a plurality of electrochemical cells, the electrochemical cells formed from (i) a first semiconductor electrode, (ii) a second semiconductor electrode, and an electrolyte in contact with the first and second semiconductor electrodes of respective electrochemical cells.

An electrochemical apparatus can include a plurality of electrochemical cells connected in series, the electrochemical cells including a first electrode and a second electrode, at least one of the electrodes comprising a material selected so as to undergo a change in resistivity upon contacting the pollutants, and an electrolyte in contact with the first and second electrodes of respective electrochemical cells. The emission sensor can include an electrochemical cell, the electrochemical cell including (i) a first semiconductor electrode, the semiconductor electrode comprising a first semiconductor material selected so as to undergo a change in resistivity upon contacting CO, wherein the first semiconductor material is $TiO_2$, $TYPd_5$, $MoO_3$, $ZnMoO_4$ or $WR_3$, (ii) a second electrode, and (iii) an electrolyte in contact with the first and second electrodes.

A method of forming a solid state electrochemical cell for measuring the concentration of a component of a gas mixture includes the steps of forming a first semiconductor electrode and a second semiconductor electrode, the electrodes comprising first and second semiconductor materials, the materials selected so as to undergo a change in resistivity upon contacting the component. An electrolyte is formed, the electrolyte being in contact with the first and second semiconductor electrodes.

A method for controlling a chemical process can include the steps of providing an electrochemical cell including (i) a first semiconductor electrode and a (ii) a second semiconductor electrode, the electrodes comprising first and second semiconductor materials, respectively. The materials are selected so as to undergo a change in resistivity upon contacting gas emitted by the chemical process. An (iii) electrolyte is provided in contact with the first and second semiconductor electrodes. The concentration of at least one gas emitted during operation of the chemical process is electrochemically determined. Chemical process conditions are adjusted based on concentrations of the gas determined in the determining step. The chemical process can be a combustion process. Preferably, the first semiconductor material exhibits a voltage response opposite in slope direction, the response being a function of detected gas concentration, to that of the second semiconductor material, whereby a voltage signal measured across the electrodes is substantially equal to the sum of the absolute values of individual voltage responses of the electrodes.

A solid state electrochemical cell for measuring the concentration of NO in a gas mixture includes a first semiconductor electrode comprising $La_2CuO_4$, a second electrode and an electrolyte in contact with the first and second electrodes. The second electrode can include Pt, while the electrolyte can comprise $ZrO_2$, $Bi_2O_3$ or $CeO_2$. A method for measuring the concentration of NO in a gas mixture includes the steps of exposing the gas mixture to a solid state electrochemical cell, the electrochemical cell formed from (i) a semiconductor electrode comprising $La_2CuO_4$ which undergoes a change in resistivity upon contacting NO, (ii) a second electrode, and (iii) an electrolyte in contact with the first and second electrodes. An electrical signal generated by the electrochemical cell is measured and used to determine the concentration of NO in the gas mixture.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

Figure 1A:
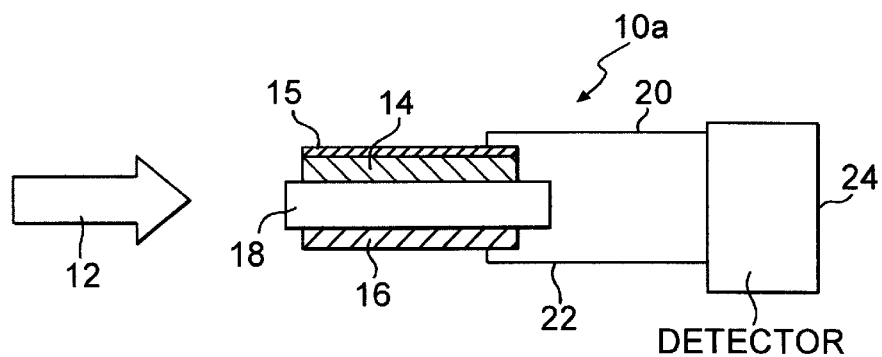
FIGS. 1A, 1B, and 1C schematically illustrate first, second, and third embodiments of a solid state electrochemical cell as disclosed herein.

As used in the specification and the appended claims, the singular forms "a", "an" and "the" include plural referents unless the context clearly dictates otherwise. Thus, for example, reference to "a semiconducting material" includes mixtures of semiconducting materials, reference to "an electrolyte material" includes mixtures of two or more electrolyte materials, reference to "an electrode" includes two or more such electrodes, and the like.

In this specification and in the claims which follow, reference will be made to a number of terms which shall be defined herein to have the following meanings:

The term "gas mixture" is used to refer to a gas containing one or more components to which the sensor is exposed during operation. A gas mixture may be, for example, the exhaust gas from an internal combustion engine containing a plurality of pollutant gases or from a furnace or other source.

The term "electrolyte" is used in its conventional sense to indicate a nonmetallic conductor in which electrical current is carried by the movement of ions. For example, an "oxygen ion-conducting electrolyte" is one in which electrical current is carried by oxygen ions.

The term "semiconductor" or "semiconducting material" is used herein in its usual sense to indicate a crystalline or polycrystalline solid material with an electrical conductivity intermediate between that of a conductor and an insulator. A summary of the physics and properties of semiconductors can be found in, for example, Sze (1981) *Physics of Semiconductor Devices,* 2nd edn., John Wiley & Sons (New York), the disclosure of which is incorporated herein by reference.

The phrase "electrochemical cell" and the term "sensor" are used interchangeably herein to mean a device for measuring the concentration of one or more gaseous materials.

Referring now to the drawings, wherein like reference numbers designate corresponding parts throughout the several embodiments, sensors 1A, 1B and 1C shown in FIG. 1 are disposed to receive a stream of a gas mixture 12, such as exhaust or emission from an engine or furnace and for measuring the concentration of a component in the gas mixture, including but not limited to $NO_x$, $CO_x$, $SO_x$, or the like.

In one embodiment shown in FIG. 1A, sensor 10a includes an electrochemical cell defined by a first electrode 14 and a second electrode 16 and an electrolyte 18 in contact with electrodes 14 and 16. As shown in FIG. 1A, as well in FIG. 1B and FIG. 1C, the electrolyte is disposed between the electrodes. However, both electrodes 14 and 16 may be situated on the same surface of the electrolyte, or other arrangements provided electrolyte 18 is in electrical contact with electrodes 14 and 16. Sensor 10a is configured so that when electrode 14 is exposed to the gas stream 12, electrode 16 is also exposed to the gas stream as well.

At least one electrode from 14 and 16 is preferably a semiconductor electrode, formed from a semiconducting material. The semiconducting material may be an n-type or a p-type semiconducting material. The semiconducting material is selected to undergo a change in conductivity or resistivity upon contacting the component of interest in the gas mixture.

The semiconductor material is preferably a metal oxide or a metal oxide compound. The terms "metal oxide" and "metal oxide compound" are used interchangeably herein to mean a compound having elemental metal combined with $O_2$. Examples of metal oxides that are useful in the invention include $SnO_2$, $TiO_2$, $TYPd_5$ (defined previously), $MoO_3$, $ZnMoO_4$ (ZM) and $WO_3$ and $WR_3$ (defined previously), $La_2CuO_4$, and mixtures thereof.

The choice of material for semiconductor electrodes is determined by the component of the gas mixture to be measured. Materials that are selectively responsive, being those that undergo a change in resistance to particular gases, are well known in the art. For example, to measure the concentration of CO in a gas mixture, semiconductor electrodes can comprise $SnO_2$, ZnO, $In_2O_3$, and mixtures thereof, optionally containing other metals or metal oxides added to enhance CO selectivity (Yamaura et al. (1996) *J. Electrochem. Soc.* 143:L36 ($In_2O_3$ with $Rb_2O$), Fukui et al. (1995) *Sensors and Actuators B* 24–25:486 ($SnO_2$ with Au—$La_2O_3$); and Nitta et al. (1979) *J. Electronic Materials* 8:571 ($SnO_2$ with $ThO_2$)). $SO_2$ may be measured using a metal sulfate such as $Li_2SO_4$, $Li_2SO_4$—$CaSO_4$—$SiO_2$ (4:4:2 in molar ratio) or $Li_2SO_4$—MgO (8:2) for semiconductor electrode 14 (Yan et al. (1966) J. Electrochem. Soc. 143:609). The above references are incorporated by reference herein.

An electrochemical cell according to the invention is believed to function by the following mechanism. A gas is absorbed on a semiconducting electrode that, depending on whether the adsorbed species is positively charged or negatively charged, results in the injection or removal, respectively, of electrons. For a p-type semiconductor, injection of electrons into the semiconductor will increase the resistance of the material and removal of electrons will decrease the resistance of the material. An n-type semiconductor has the opposite response.

When a semiconducting electrode and another electrode (opposing electrode) are both placed in contact with an appropriate electrolyte, injection of electrons into the semiconducting electrode will increase the potential (voltage) of that electrode relative to the opposing electrode. Removal of electrons from the semiconducting electrode will decrease the potential of the semiconducting electrode. In contrast to a semiconducting electrode, a metal electrode in contact with an electrolyte will have no measurable change in potential from injection or removal of electrons.

In fact, metal electrodes will only react to changes in oxygen partial pressure ("$pO_2$") in the gas mixture, thereby acting as a relative reference, or equilibrium, electrode. Thus, an electrochemical cell deriving a signal taken across a semiconducting electrode and a metal electrode will have a selective response, the response being that of the semiconducting electrode in the presence of a particular adsorbed gas. Unlike sensors described in the art that depend on the selective catalytic reduction, decomposition or other change in state of the gases to be measured, electrochemical sensors according to the invention are believed to function without catalytic alteration of components of the gas mixture.

In operation of the sensor, a calibration curve of (voltage) signal versus concentration is preferably first derived with the input of a calibrated gas mixture containing the component(s) of interest. Data obtained, such as generated voltage data, can be stored in a suitable memory device. A calibration is preferably a performed over a range of temperatures and gas mixtures of interest. In actual operation, the set of calibration curves are preferably stored in a suitable non-volatile memory and are compared against the electrical data derived from the electrochemical sensor to determine the concentration of one or more components of interest. It may also be possible to generate calibration curves using various simulation tools.

A metal electrode can provide an equilibrium reference between the conductive ions and the corresponding gas, e.g., oxygen ions and $O_2$. In addition, a metal electrode can serve as an electronic conductor to complete the circuit necessary to measure the electrical characteristic output by the sensor. Metal electrodes are preferably formed from silver, gold, rhodium, or a noble metal such as platinum.

The choice of material for electrolyte 18 depends on the component in the gas mixture to be measured. Thus, to measure the concentration of an oxide component, for example, $NO_x$, $CO_x$ or $SO_x$ the electrolyte is preferably an oxygen-ion conducting electrolyte. Preferred oxygen ion-conducting electrolytes are electrolyte mixtures based on zirconia ($ZrO_2$), bismuth oxide ($Bi_2O_3$), and ceria ($CeO_2$). Practical electrolyte mixtures generally include one or more dopants, such as calcia (CaO) and yttria ($Y_2O_3$), or some other suitable oxygen ion-permeable material.

Electrodes 14 and 16 are respectively connected by leads 20 and 22 to a suitable detector 24 that measures an electrical characteristic, e.g., the voltage or current, generated by the electrochemical cell. The measured electrical characteristic, such as voltage, is roughly proportional to the concentration of the component in the gas mixture.

A portion of semiconductor electrodes can be optionally coated with at least one metal layer 15 as shown in FIG. 1A. The presence of a metal layer on semiconductor electrodes can increase the signal-to-noise ratio and result in enhanced sensitivity with respect to the component of the gas mixture being measured. The metal layer 15 can be, for example, silver, gold, rhodium, or a noble metal such as platinum, as described above with respect to metal electrodes. The metal layer 15 may be coterminous with a semiconductor electrode or may be applied to semiconductor electrode at the point of attachment of lead. The metal layer 15 need not cover the entire exposed surface of a semiconductor electrode and may cover as little as about 2 percent to about 50 percent of the exposed surface.

The metal layer 15 may cover more than 50 percent, preferably 90 percent and more preferably 100 percent of the exposed surface of a semiconductor electrode. Furthermore, the metal layer 15 need not be a continuous layer of metal on the exposed surface of semiconductor electrode, but may be formed in any pattern desired. e.g., a cross-hatch pattern, a serpentine pattern, a dotted pattern, or the like, or even a random pattern. The metal layer 15 may be applied to semiconductor electrodes using any method well known in the art to achieve a layer thickness of about 1 $\mu$m to about 1000 $\mu$m, preferably about 50 $\mu$m to about 500 $\mu$m, and more preferably about 100 $\mu$m to about 250 $\mu$m.

Figure 1B:
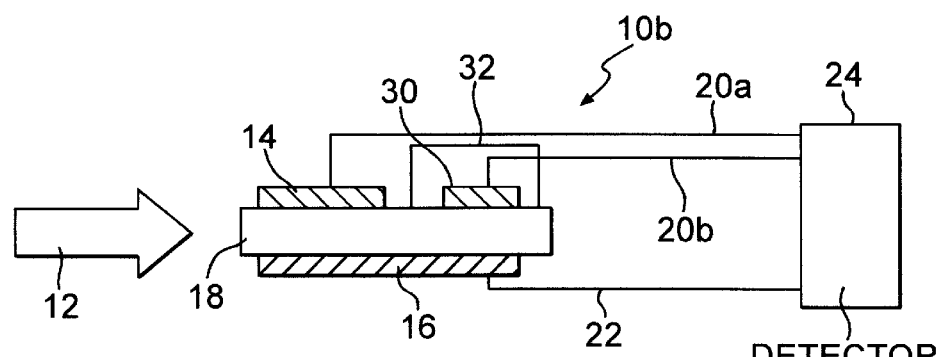

In a second configuration, illustrated in FIG. 1B, a multifunctional sensor 10b is shown including reference electrode 30. A reference electrode 30 is preferably included for a number of applications. For example, a reference electrode is generally required for a multi-gas sensor where one of the gasses is $O_2$. Also, a reference electrode can be useful with certain gasses to provide an absolute voltage value, instead of a relative value.

Reference electrode 30 can be encased in sealed chamber 32 so as not to contact the gas mixture to which electrodes 14 and 16 are exposed. An electrical characteristic of reference electrode 30 relative to electrode 16 is measured by connecting the electrodes to an appropriate detecting device such as 24, which may or may not be the same device 24 to which electrodes 14 and 16 are connected. The composition of reference electrode 30 is selected to allow measurement of a selected gas component of the gas mixture. For example, to measure the concentration of oxygen in the gas mixture using the reference electrode, i.e., the partial pressure of oxygen ("$pO_2$"), reference electrode 30 is composed of a mixture of a metal and the corresponding metal oxide, for example, Ni/NiO, Cu/CuO, or the like.

Figure 1C:
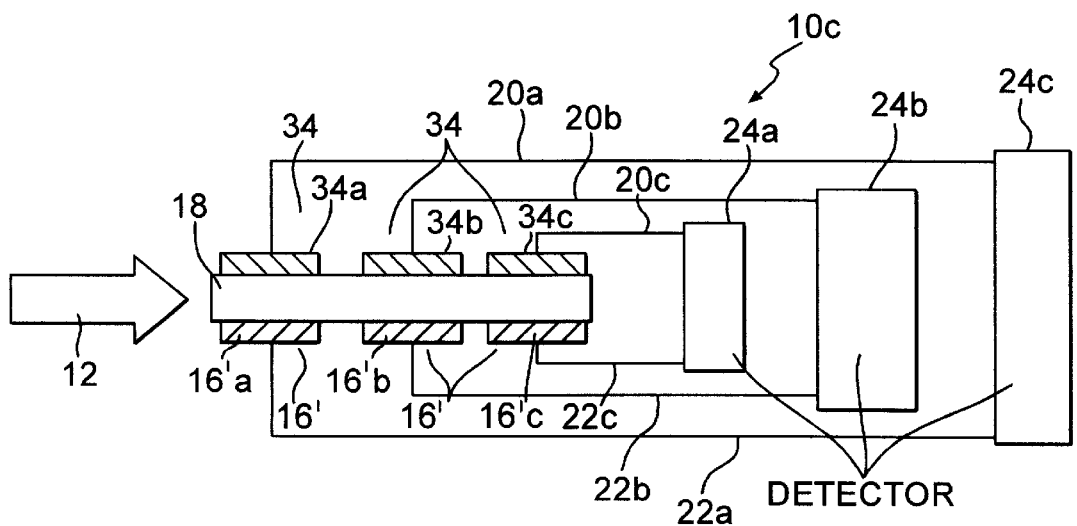

An additional embodiment of the invention is illustrated in FIG. 1C. Multifunctional sensor shown generally at 10c includes a plurality of electrochemical cells, formed from a plurality of electrodes. A set of electrodes 34, such as 34a, 34b and 34c, each of which can be a semiconducting material that undergoes a change in conductivity or resistivity upon contacting one or more desired components of the gas stream 12. Each of the set of electrodes 34 is preferably chosen to be selectively responsive to a particular component of the gas mixture, thereby allowing the simultaneous measurement of the concentration of more than one component of the gas mixture. Thus, assuming electrodes 34a, 34b and 34c are semiconductor electrodes, electrodes 34a, 34b, and 34c may be $La_2CuO_4$, $WR_3$, and $In_2O_3$ doped with $Rb_2O$ and $Li_2SO_4$—MgO (8:2), respectively, and allow the simultaneous measurement of NO, CO and $SO_2$. In this embodiment, a portion of semiconductor electrodes 34a, 34b, and/or 34c can be coated with a metal layer as described in detail above.

Also shown in FIG. 1C is an alternate configuration of electrode 16'. In this configuration, electrode 16' comprises a plurality of discrete electrodes 16'a, 16'b, and 16'c that may be formed from the same or different materials. Thus, for example, electrodes 16'a, 16'b, and 16'c may be the same or different metals, or the same or different semiconductors and may be respectively paired with semiconductor electrodes 34a, 34b, and $3^4c$ to form three electrochemical cells. The electrochemical characteristic of choice for each electrochemical cell thus formed may be individually monitored by separate detectors 24a, 24b, 24c, respectively. In addition, a separate chamber-encased reference electrode as described above can be incorporated into sensor 10c (not shown) to provide for the measurement of an additional component of the gas mixture.

In the preferred embodiment, electrodes 16' and 34 are both semiconductor electrodes for enhanced sensitivity. If CO is to be monitored, at least one electrode 16' and 34 should preferably be formed from $SnO_2$, $TiO_2$, $TYPd_5$, $MoO_3$, $ZnMoO_4$ and $WR_3$ If NO is to be monitored, it is preferred that one electrode (16' or 34) is formed from $La_2CuO_4$.

The electrolyte 18 of the sensor may be fabricated using conventional ceramic processing techniques. Electrode materials may be applied to the surface of the electrolyte using any of a variety of methods well known in the art including sputtering, screen printing, dipping, painting, and the like. Each electrode incorporates an electrical lead by which it can be attached to a monitoring device, such as detector 24.

Optionally, a temperature control device capable of providing temperature regulation thereof is incorporated in the sensor apparatus. Preferably the temperature control device comprises a heating element, such as a resistive wire, that is incorporated into the electrolyte or on the surface of the electrolyte, to which a power source is connected. Any suitable heating element known can be used. A cooling structure may also be included used with the invention. Addition of a cooling structure is expected to be particularly helpful if the gas to be measured is very hot, such as 800° C. or more, and it is desired to cool the gas to a lower temperature, such as 400–700° C., prior to measurement.

In the preferred embodiment of the invention, electrochemical cells are formed from two semiconductor electrodes, the semiconductor electrodes comprising the respective electrochemical cells contacting a common electrolyte. The first and second semiconductor electrode materials have voltage responses, the response being functions of detected gas concentration, opposite in slope direction to each other, whereby a voltage signal measured across the first and second electrodes is substantially equal to the sum of the absolute values of individual voltage responses of the first and second semiconductor electrodes. Thus, through choice of a first semiconducting electrode having a positive response (increasing potential upon gas exposure), while selecting a second electrode having a negative response (decreasing potential upon gas exposure) to the same gas, the detected response taken across the two respective electrodes is nearly additive, this increasing the signal generated by the electrochemical device. For example, if a first semiconductor electrode exhibits a −90 mv response relative to a fixed reference electrode to a given set of conditions with respect to a given gas component, while a second semiconductor electrode is selected which exhibits a +60 mv response relative to the fixed reference electrode under the same set of conditions with respect to the gas component, a 150 mv signal can be measured across the first and second electrodes. Higher signal levels can be expected to improve the signal to noise ratio output by the electrochemical cell.

In addition, signal strength may also be increased by connecting two or more electrochemical sensors in a series connection. Series connection of a plurality of electrochemical sensors can provide sensor responses having amplitudes which permit improved detection of gas components. having low level signals, when the response of a single sensor may not be sufficient to detect the same. See FIG. 15. For example, a given electrochemical apparatus can be formed from N electrochemical cells, each electrochemical cell including a semiconducting electrode and a metal electrode, or two semiconducting electrodes. In the case of cells formed from a semiconducting electrode and a metal electrode, the electrochemical apparatus can be configured by connecting semiconductor electrodes to metal electrodes of adjacent electrochemical cells.

The operation of an electrochemical apparatus formed from a series connection of electrochemical cells can be distinguished from a series connection of cells in devices, such as batteries or fuel cells. In fuel cells and batteries, the cell configuration is anode/electrolyte/cathode which is repeated in the stack with anodes electrically connected to cathodes of neighboring cells. The anode and cathode each require a distinctly different source of chemical energy that must be kept separate. For example, a fuel cell anode is provided fuel, such as hydrogen, while the cathode is provided an oxygen containing gas, such as air.

In contrast, in the electrochemical apparatus formed from a series connection of electrochemical cells, the two electrodes of each cell are exposed to the same gas stream with no requirement for gas stream separation. In fact both electrodes can be on the same side of the electrolyte. Because of this design flexibility possible with the invention, there are numerous interdigitated configurations of electrodes that can be used that cannot be utilized with a fuel cell or battery.

Moreover, since fuel cells and batteries are used to produce electric power (current multiplied by voltage), the size of the electrodes needs to be maximized to produce sufficient current, the current being proportional to electrode area. However, in a potentiometric sensor such as the sensor described herein, current generation is not necessary because only a voltage is measured. Voltage, unlike current, is independent of electrode area. Therefore, a very small sensor with a plurality of nano-electrodes can be configured to produce a very large voltage output. In contrast, a fuel cell or battery with numerous nano-electrodes would produce no more power (the desired output) than a single large electrode of the same total area.

Sensors according to the invention can be used to improve the performance of devices or create devices having new capabilities. For example, the invention can be used as a sensor in a feedback control system to improve operation of gas turbines, coal fired power plants and boilers. By electrochemically determining the concentration of at least one gas emitted during operation of a chemical process, such as a process performed at a chemical processing plant, and adjusting chemical process conditions based on concentrations of said gas determined, the performance of the chemical process being monitored can be improved. The invention can be used for various monitors, such as for the monitoring of gasses in environmental monitoring applications.

The invention is useful for internal combustion engines where it can be used to monitor emitted pollutants, such as CO and NO. By coupling sensors according to the invention with appropriate feedback control systems known in the art, emissions can be reduced and fuel economy increased. Although potentiometric $O_2$ sensors have been used to control the air/fuel ratio in combustion engines for years, sensors are not currently used to measure the concentration of actual pollutants emitted in the exhaust stream. Through measurement of exhaust pollutants such as CO and the use of appropriate feedback control systems, emissions can be reduced and fuel economy increased beyond the levels provided by existing $O_2$ sensors.

In a related embodiment of the invention, an internal combustion engine 1610 has at least one cylinder (not shown), the cylinder for combusting a fuel mixture therein. The internal combustion engine 1610 can power a motor vehicle, such as an automobile, in whole or in part. An electrochemical emission sensor 1620 is disposed in the exhaust stream 1630 to receive the emitted gas mixture including pollutants and for determining the concentration of at least one pollutant component from the exhaust stream. A feedback and control system 1640, such as those currently used in conjunction with $O_2$ sensors, can receive pollutant concentration data from the emission sensor 1620 and automatically direct adjustment of combustion conditions, such as the air/fuel mixture using air control device 1650 and fuel control device 1660, responsive to the measured pollutant concentration. In the preferred embodiment of the invention, the sensor provided 1620 is sensitive to CO over a range of concentrations generally emitted by most motor vehicle engines during operation.

The sensor dimensions can be varied across a large range of dimensions. Using conventional screen printing the electrodes could be made to be approximately 1 cm×1 cm, to as small as 0.1 mm×0.1 mm. However, using semiconductor lithographic and etching processes, the sensor dimensions produced could be on the order of microns, or could be submicron.

Electrochemical cells will generally be assembled into a package. For exhaust monitoring applications, the packaging used generally requires an electrical lead feedthrough and a seal between the exhaust and ambient. Air quality monitoring may not require a seal. In most applications, choice of a packaging material adapted to withstand temperatures of up to 800° C. or more is required.

EXAMPLES

Unless indicated otherwise, parts are parts by volume, temperature is in ° C. and pressure is at or near atmospheric pressure. Potentiometric sensors in the following formats were studied and the results obtained are summarized below:

| ELECTROCHEMICAL CELL | CELL NUMBER |
| --- | --- |
| (CO + air), $TiO_2$, Au/SE/Au, (CO + air) | (I) |
| (CO + air), $TYPd_5$, Au/SE/Au, (CO + air) | (II) |
| (CO + air), $TiO_2$, Au/SE/$TYPd_5$, Au, (CO + air) | (III) |
| (CO + air), ZM, Au/SE/Au, (CO + air) | (IV) |
| (CO + air), $WR_3$, Au/SE/Au, (CO + air) | (V) |
| (CO + air), $MoO_3$, Au/SE/$SnO_2$, Au, (CO + air) | (VI) | where: SE = Solid Electrolyte; yttria stabilized zirconia (YSZ)

The performance of the above cells was evaluated in terms of the potential (EMF), response time, reversibility, recovery characteristics, and temperature dependence of the signals obtained.

Figure 2:
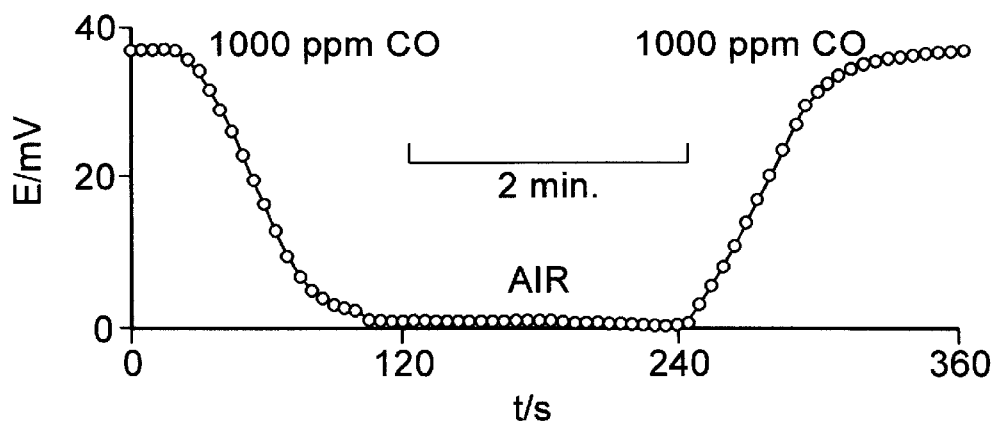
FIG. 2 illustrates the speed and recovery characteristic of a potentiometric cell formed from $TiO_2$ and $TYPd_5$ electrodes resulting from a 1000 ppm CO concentration step.

Rapid response and recovery characteristics of electrochemical cell III, comprising a $TiO_2$ semiconducting electrode and a $TYPd_5$ semiconducting electrode, is shown in FIG. 2 for a 1000 ppm CO concentration step at 600° C. The response time is defined as the time required to reach 90% of the steady value ($t_{90}$). At a typical temperature of 600° C., the response time was about 1 minute for a 1000 ppm CO step, while the recovery time for the sensor to attain the initial value when the CO was shut-off, was less than 2 minutes.

Figure 3:
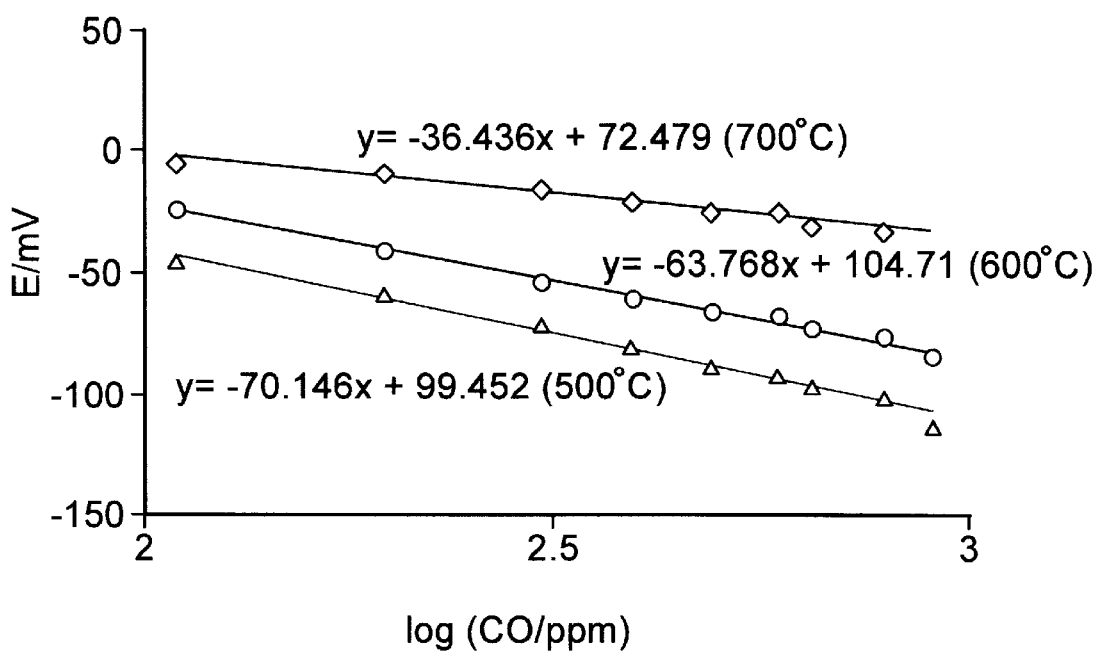
FIG. 3 illustrates linear dependence of voltage vs. log (CO) concentration of a potentiometric cell using $TiO_2$ as the sensing electrode and gold as the opposing electrode.

FIG. 3 shows the variation of voltage of cell I, comprising a $TiO_2$ semiconducting electrode and a gold electrode, as a function of CO concentration (up to 1000 ppm) in the temperature range of 500–700° C. A dependence of voltage on logarithmic CO concentration is shown to be substantially linear, constituting a Nernstian relation. With increasing temperature, the signal magnitude becomes systematically smaller signifying the effect of diminished adsorption of CO on the semiconducting oxide surface at higher temperatures.

Figure 4:
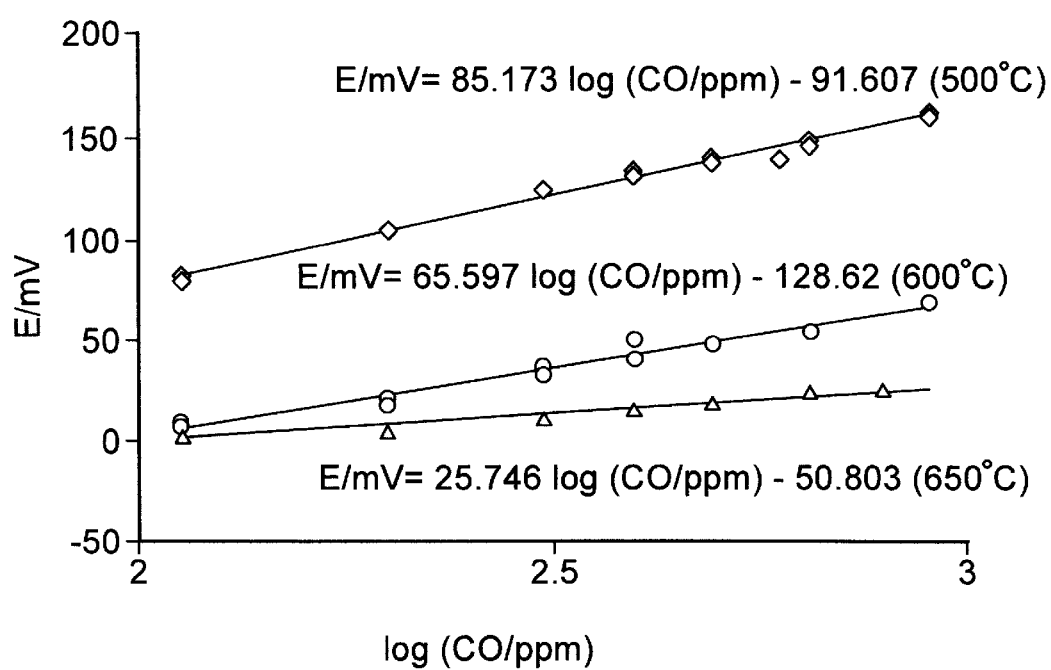
FIG. 4 illustrates isothermal plots of voltage vs. log (CO) concentration of a potentiometric cell formed using a $TYPd_5$ composite as the sensing electrode and gold as the opposing electrode.

Isothermal plots of the voltage developed in cell II comprising a $TYPd_5$ semiconducting electrode as the sensing electrode and a gold opposing electrode for CO concentrations from 100 to 1000 ppm at temperatures of 500, 600 and 650° C. are shown in FIG. 4. While the slope of the voltage generated to log(CO concentration) shown in FIG. 3 is negative, the slope of the same quantity shown in FIG. 4 has a positive slope. This shows that the behavior of the two semiconductor oxides $TiO_2$ and $TYPd_5$ are opposite in nature.

Figure 5:
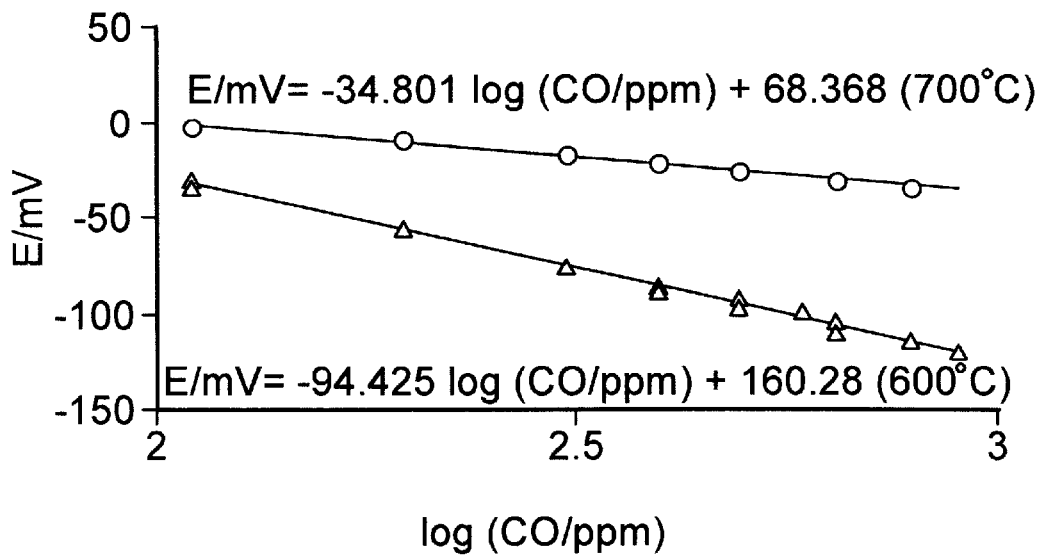
FIG. 5 illustrates linear voltage vs. log (CO) concentration of a potentiometric cell using $TiO_2$ and $TYPd_5$ electrodes.

Cell III is formed by combining the semiconducting sensing electrodes used to generate data shown in FIGS. 3 and 4 into a single electrochemical cell. The voltage response as a function of detected CO concentration of cell III is shown in FIG. 5. The response is essentially an algebraic sum of the absolute values of the responses of the first two cells. Thus, by forming an electrochemical cell having $TiO_2$ and $TYPd_5$ electrodes, the voltage signal developed across the $TiO_2$ and $TYPd_5$ electrodes is the sum of the individual responses of the respective semiconducting electrodes with reference to a metal electrode.

For example, at 600° C. the electrode potential of cells I and II for 100 ppm CO was −23 and +3 mV, respectively. Under identical conditions, a voltage of +28 mV was recorded in cell III, which is in excellent agreement with the algebraic sum of the respective responses of the semiconducting electrodes comprising cell II. The response shown by the electrochemical cell formed from the two semiconducting oxide electrodes shown in FIG. 5 also decreases with an increase in experimental temperature, as was seen in FIGS. 3 and 4 for cells I and II, respectively. Therefore, by identifying electrode materials having voltage responses, the responses being functions of detected gas concentration, to a given component with opposite polarity slopes, the overall sensitivity of potentiometric cells using two such oxide electrodes can be enhanced.

Figure 6:
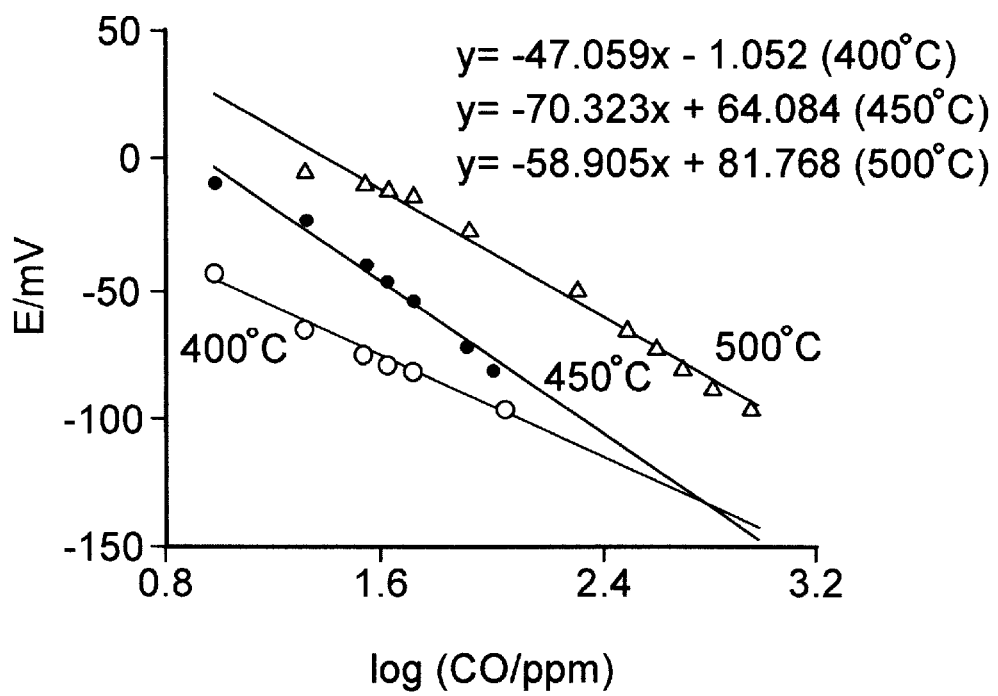
FIG. 6 illustrates linear voltage vs. log (CO) concentration of a potentiometric cell using $ZnMoO_4$ as the sensing electrode at 400–500° C. and gold as the opposing electrode.

FIG. 6 shows semi-log linear behavior of cell IV. Cell IV comprises a $ZnMoO_4$ (ZM) sensing electrode and a gold opposing electrode. Data is provided at 400, 450 and 500° C.

Figure 7:
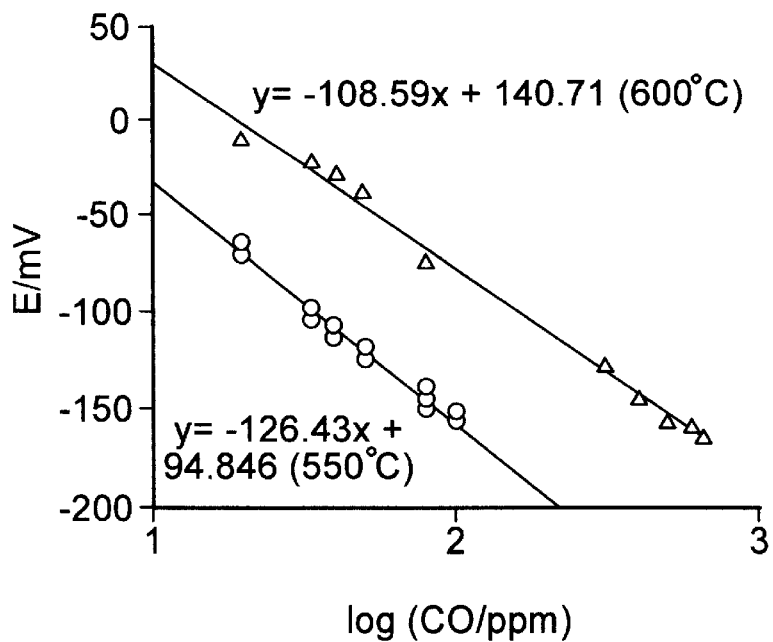
FIG. 7 illustrates CO dependence of the EMF in a potentiometric cell using $WR_3$ as the sensing electrode and gold as the opposing electrode.

The sensing characteristics of cell V, comprising $WR_3$ is shown in FIG. 7. Linear correlation between the log (CO concentration) and the resulting electrochemical potential is shown in the range of about 10–700 ppm using a $WR_3$ sensing electrode.

Figure 8:
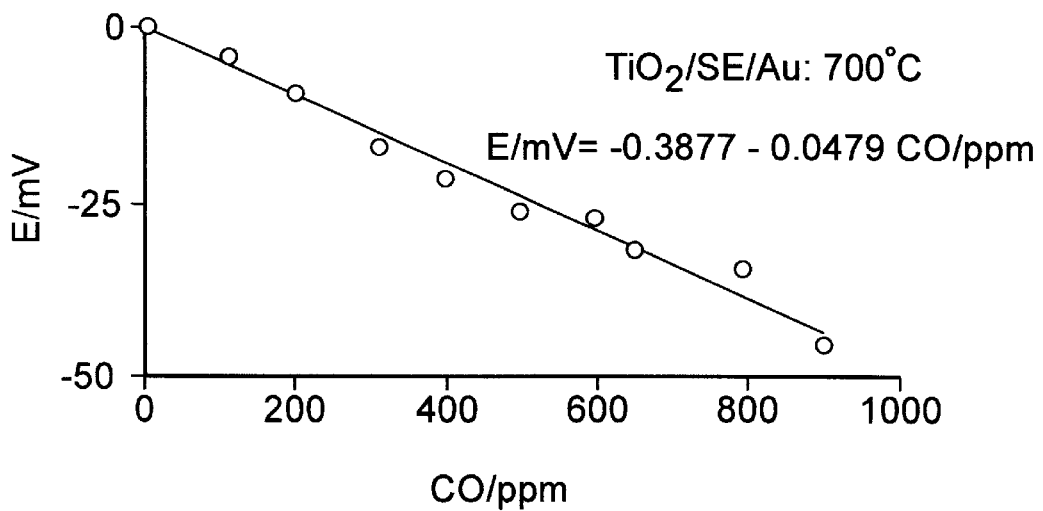
FIG. 8 illustrates linear dependence of voltage vs. CO concentration in a potentiometric cell using $TiO_2$ as the sensing electrode and gold as the opposing electrode at 700° C.
Figure 9:
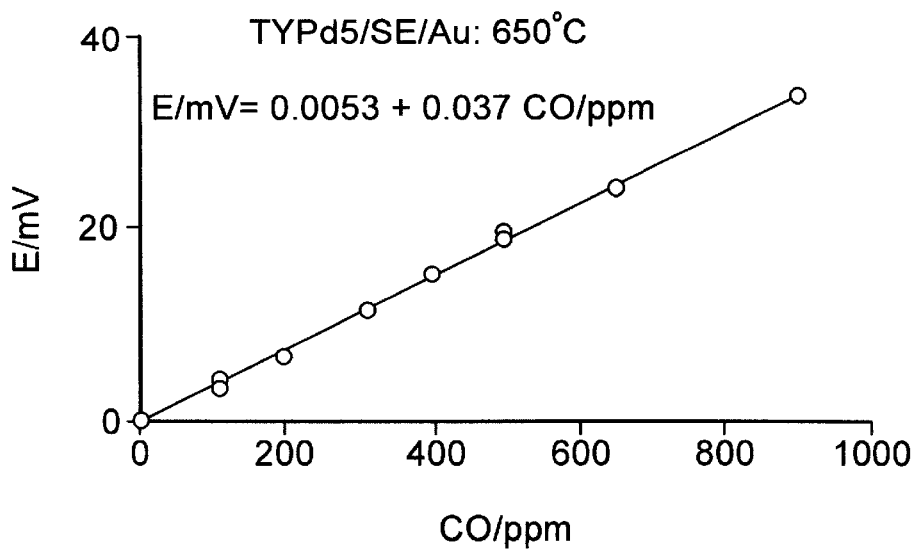
FIG. 9 illustrates linear dependence of voltage vs. CO concentration in a potentiometric cell formed from $TYPd_5$ as the sensing electrode and gold as the opposing electrode at 650° C.

At higher temperatures, the dependence of voltage on CO concentration was found to switch from logarithmic to linear. FIG. 8 shows a linear relationship for cell I ($TiO_2$ sensing electrode) at 700° C, while FIG. 9 shows the resulting linear relationship for cell II ($TYPd_5$) at 650° C.

Figure 10:
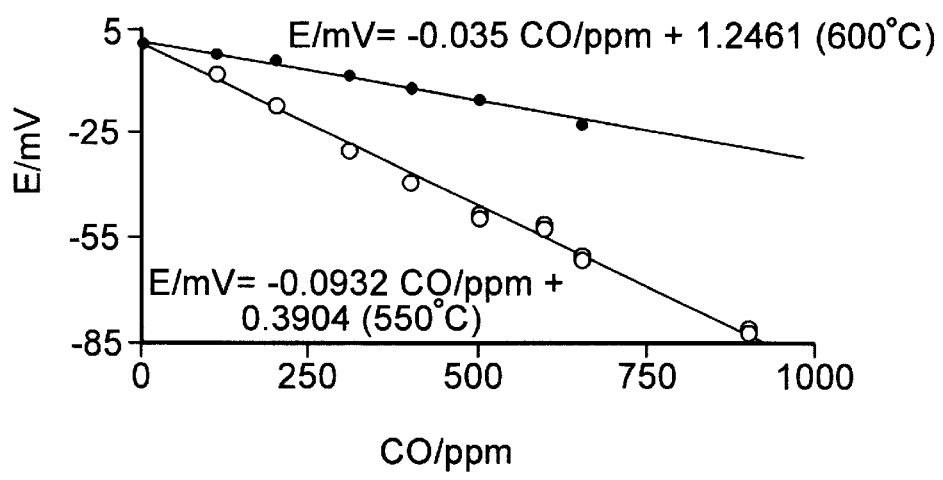
FIG. 10 illustrates the linear relationship between the EMF generated and the CO levels at higher temperatures in a potentiometric cell using a $ZnMoO_4$ sensing electrode and a gold opposing electrode.

Similar behavior is shown in FIG. 10 in the case of cell IV (ZM sensing electrode) where Nernstian linearity changes to a simple linear relationship between the observed voltage and CO concentration as the temperature is raised to 550° C. and 600° C., respectively. The signals also show stability as a function of time.

Figure 11:
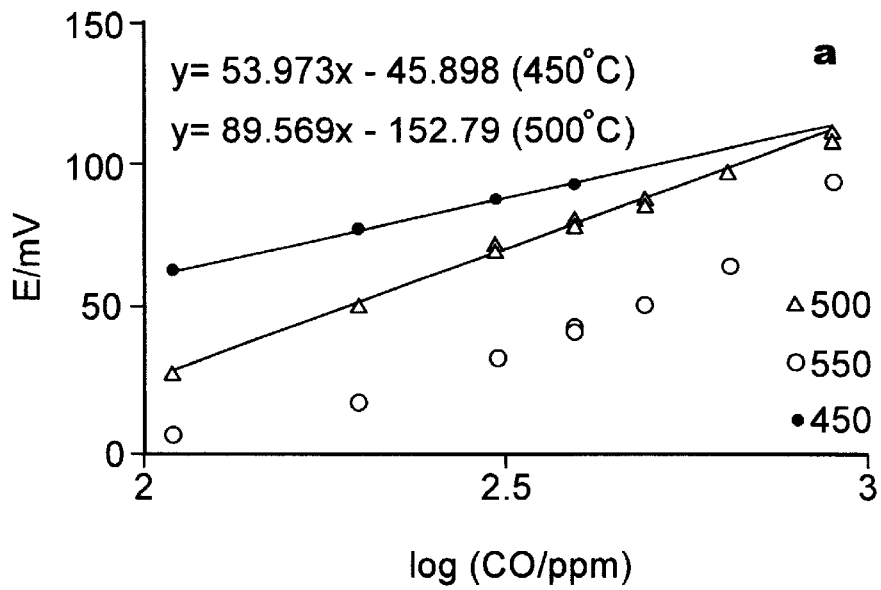
FIG. 11 illustrates Nernstian linearity for temperatures up to 500° C. between the electrode potential and log (CO) generated by a potentiometric cell using $MoO_3$ and $SnO_2$ electrodes.
Figure 12:
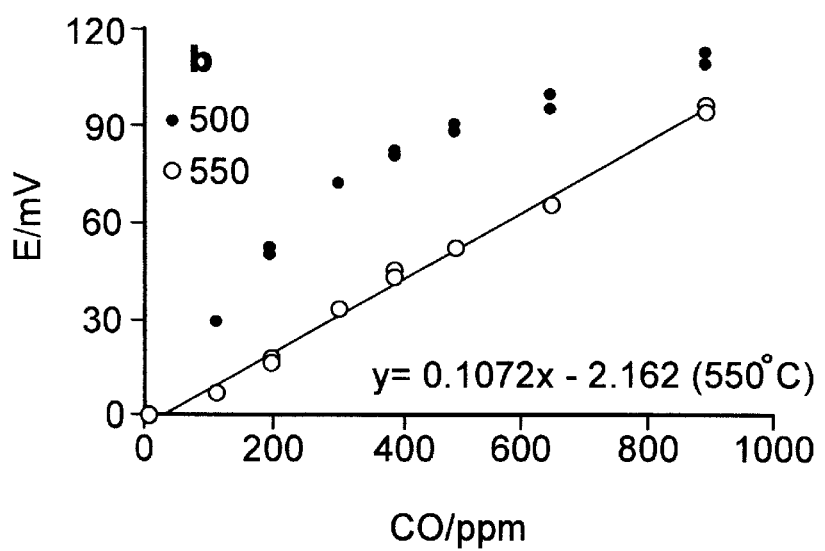
FIG. 12 illustrates linear dependence of EMF on CO concentration at 550° C. generated by a potentiometric cell having $MoO_3$ and $SnO_2$ electrodes.
Figures 13, 14:
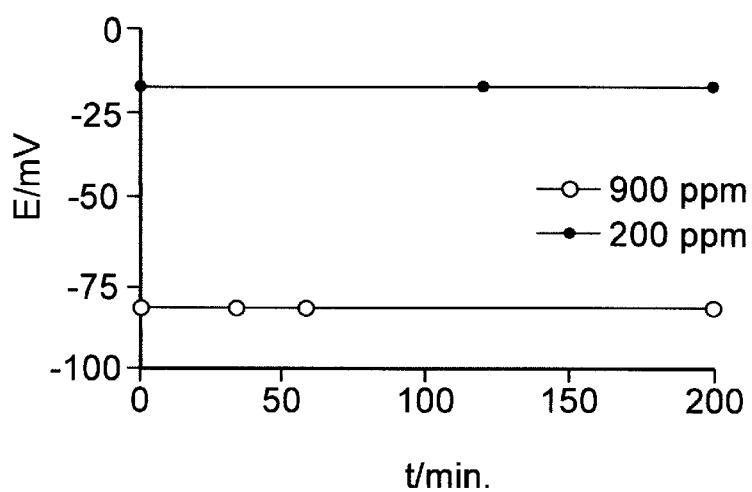
FIG. 13 illustrates the stability of the signal generated by a potentiometric cell using $MoO_3$ and $SnO_2$ electrodes as a function of time when exposed to CO at 550° C.
FIG. 14 illustrates a table summarizing the performance of various semiconductor oxide electrodes in terms of sensitivity to CO.

FIG. 11 shows Nernstian linearity between the electrode potential and log (CO) for cell VI ($SnO_2$ and $MoO_3$ sensing electrodes) at temperatures of 450° C. and 500° C. FIG. 12 shows a simple linear dependence of EMF on CO concentration at 550° C. for cell VI. FIG. 13 shows stability in the signal generated by cell VI at a typical temperature of 550° C. for two gas levels, 200 and 900 ppm of CO throughout a 200 minute interval.

The results obtained with various combinations of semiconducting oxides as the electrode materials are summarized in FIG. 14 in terms of sensitivity to CO. From FIG. 14, it can be readily seen that many new CO sensing electrodes materials have been identified in the invention, with appreciably large slopes in the voltage vs. log (CO) curves. Among these, the behavior of $WR_3$ is particularly good in terms of the largest slope magnitude. In addition, while, $TiO_2$ and $TYPD_5$ individually have adequate slopes, their combination gives even higher sensitivity for CO measurements.

Figure 15:
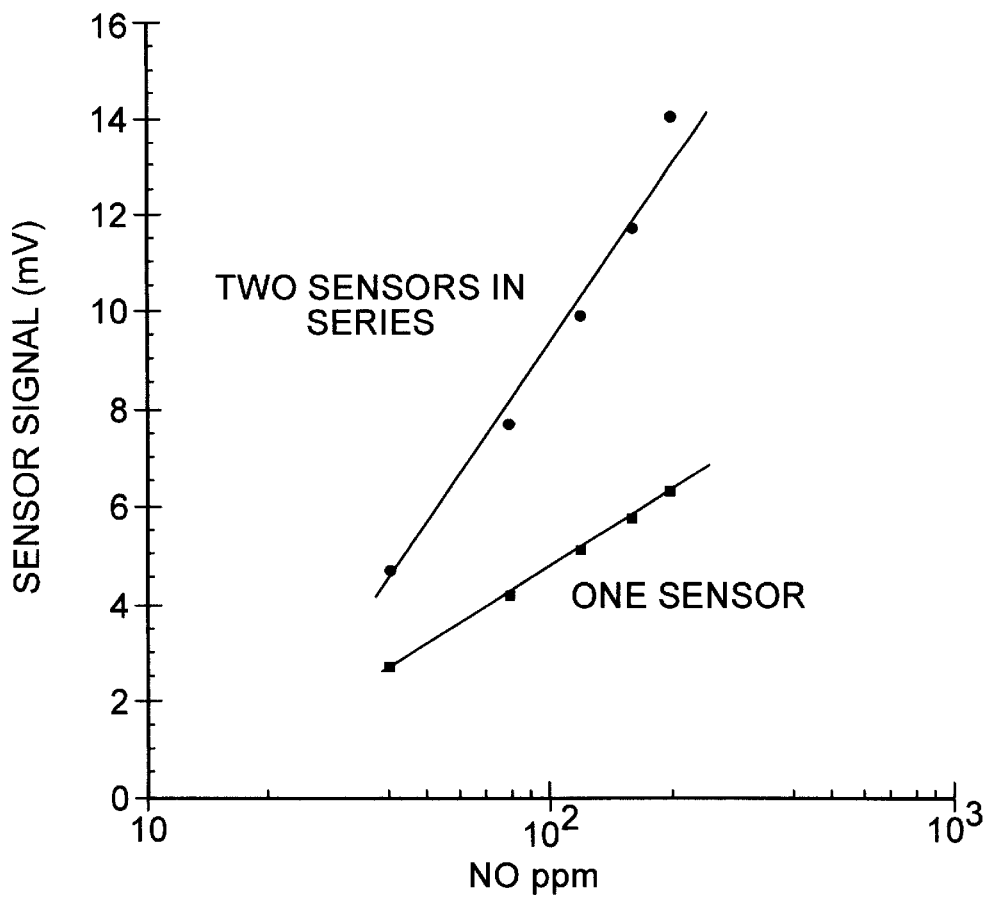
FIG. 15 shows the comparative responses of two NO sensors in series as compared to a single NO sensor using $La_2CuO_4$ and Pt electrodes at 550° C.
Figure 16:
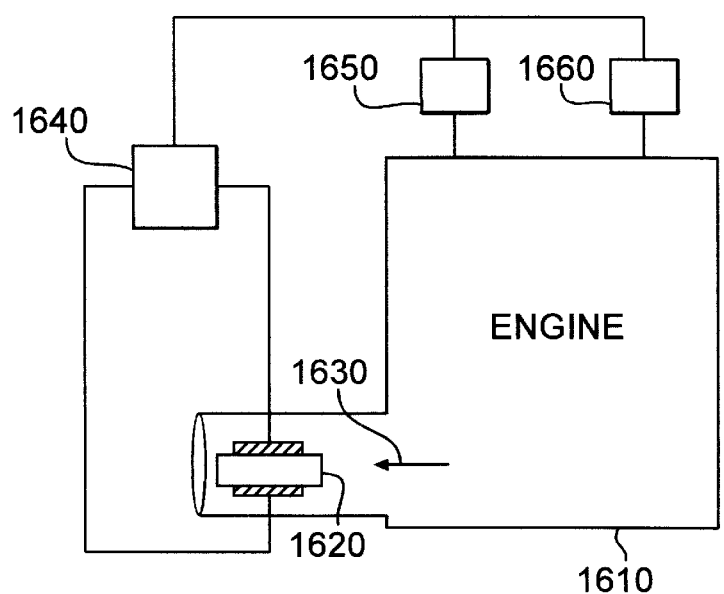
FIG. 16 illustrates a schematic of an engine including an electrochemical cell for exhaust gas sensing along with a feedback control system, according to an embodiment of the invention.

FIG. 15 shows the comparative responses of two NO sensors in series as compared to one NO sensor. The electrochemical cells were each formed from a semiconducting $La_2Cu_4$ electrode, a YSZ electrolyte and a Pt electrode. Other metal electrodes could have been substituted for Pt. The test was performed by exposing the sensors to a simulated 550° C. exhaust gas comprising 15% $O_2$, 3% $H_2O$, 10% $CO_2$, 72% $N_2$. In the range of NO concentration from 40 to 300 ppm two NO sensors connected in series produced a voltage signal having an amplitude that is approximately twice that of the single sensor device. Although FIG. 15 shows series connection of sensors to improve signal strength for NO detection, series connection of sensors can be applied generally for improved detection of other gases.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A solid state electrochemical cell for measuring the concentration of a component of a gas mixture, comprising:
   a first semiconductor electrode and a second semiconductor electrode, said electrodes comprising first and second semiconductor materials, respectively, said materials selected so as to undergo a change in resistivity upon contacting said component; and,
   an electrolyte in contact with said first and second semiconductor electrodes.

2. The electrochemical cell of claim 1, further comprising a reference electrode in contact with said electrolyte.

3. The electrochemical cell of claim 1, further comprising at least one metal layer disposed on a portion of at least one of said semiconductor electrodes.

4. The electrochemical cell of claim 1, further comprising a detector for measuring an electrical characteristic generated by said electrochemical cell.

5. The electrochemical cell of claim 1, wherein at least one of said semiconductor materials comprise a metal oxide.

6. The electrochemical cell of claim 5, wherein said metal oxides are selected from the group consisting of $SnO_2$, $TiO_2$, $TYPd_5$, $MoO_3$, $ZnMoO_4$ and $WR_3$.

7. The electrochemical cell of claim 1, wherein said first semiconductor material exhibits a voltage response when exposed to said component, said voltage response opposite in slope direction to that of said second semiconductor material.

8. The electrochemical cell of claim 1, wherein said component includes CO.

9. The electrochemical cell of claim 1, wherein said electrolyte is an oxygen ion-conducting electrolyte.

10. The electrochemical cell of claim 9, wherein said oxygen ion-conducting electrolyte comprises at least one selected from the group consisting of $ZrO_2$, $Bi_2O_3$ and $CeO_2$.

11. A solid state electrochemical cell for measuring the concentration of a component of a gas mixture, comprising:
   a first semiconductor electrode and a second semiconductor electrode, said electrodes comprising first and second semiconductor materials, respectively, said materials selected so as to undergo a change in resistivity upon contacting said component, wherein said first semiconductor material exhibits a voltage response when exposed to said component, said voltage response opposite in slope direction to that of said second semiconductor material, whereby a voltage signal measured across said electrodes is substantially equal to the sum of the absolute values of individual voltage responses of said electrodes; and, an electrolyte in contact with said first and second semiconductor electrodes.

12. A solid state electrochemical apparatus for measuring the concentration of at least two components of a gas mixture, comprising:
a plurality of electrochemical cells, said electrochemical cells each formed by two semiconductor electrodes, said semiconductor electrodes comprising semiconductor materials, respectively, said materials selected so as to undergo a change in resistivity upon contacting said at least one of said components; and,
an electrolyte in contact with said first and second semiconductor electrodes.

13. The electrochemical apparatus of claim 12, further comprising at least one metal layer disposed on a portion of at least one of said semiconductor electrodes.

14. The electrochemical apparatus of claim 12, further comprising a detector for measuring an electrical characteristic generated by said electrochemical cell.

15. The electrochemical apparatus of claim 12, wherein at least one of said semiconductor materials comprise a metal oxide.

16. The electrochemical apparatus of claim 15, wherein said metal oxides are at least one selected from the group consisting of $La_2CuO_4$, $SnO_2$, $TiO_2$, $TYPd_5$, $MoO_3$, $ZnMoO_4$ and $WR_3$.

17. The electrochemical apparatus of claim 12, wherein at least one of said plurality of electrochemical cells comprises a first electrode comprising a first semiconductor material having a voltage response when exposed to said component, said voltage response opposite in slope direction to that of said second semiconductor material, whereby a voltage signal measured across said first and second electrodes is substantially equal to the sum of the absolute values of individual voltage responses of said first and second electrodes.

18. The electrochemical apparatus of claim 12, wherein said components include at least one selected from the group consisting of CO and NO.

19. The electrochemical apparatus of claim 12, wherein said electrolyte is an oxygen ion-conducting electrolyte.

20. The electrochemical apparatus of claim 19, wherein said oxygen ion-conducting electrolyte comprises at least one selected from the group consisting of $ZrO_2$, $Bi_2O_3$ and $CeO_2$.

21. The electrochemical apparatus of claim 12, further comprising a reference electrode in contact with said electrolyte.

22. An electrochemical apparatus for measuring the concentration of a component of a gas mixture, comprising a plurality of electrochemical cells connected in series, said electrochemical cells each having a first electrode and a second electrode, at least one of said electrodes comprising a material selected so as to undergo a change in resistivity upon contacting said component; and
an electrolyte in contact with said first and second electrodes.

23. The electrochemical apparatus of claim 22, wherein at least one of said electrodes in said plurality of electrochemical cells comprise metal oxide semiconductor materials.

24. The electrochemical apparatus of claim 23, wherein said metal oxides are at least one selected from the group consisting of $La_2CuO_4$, $SnO_2$, $TiO_2$, $TYPd_5$, $MoO_3$, $ZnMoO_4$ and $WR_3$.

25. The electrochemical apparatus of claim 22, wherein each of said electrodes in said plurality of electrochemical cells comprise metal oxide semiconductor materials.

26. The electrochemical apparatus of claim 25, wherein said metal oxides are at least one selected from the group consisting of $SnO_2$, $TiO_2$, $TYPd_5$, $MoO_3$, $ZnMoO_4$ and $WR_3$.

27. The electrochemical apparatus of claim 23, further comprising at least one metal layer disposed on a portion of said metal oxide semiconductor materials.

28. The electrochemical apparatus of claim 22, further comprising a detector for measuring an electrical characteristic generated by said electrochemical apparatus.

29. The electrochemical apparatus of claim 25, wherein at least one of said electrochemical cells includes a first metal oxide semiconductor material comprising said first electrode that exhibits a voltage response when exposed to said component, said voltage response opposite in slope direction to a voltage response of different metal oxide semiconductor material which comprises said second electrode, whereby a voltage signal measured across said electrodes in said at least one electrochemical cell is substantially equal to the sum of the absolute values of individual voltage responses of said electrodes.

30. The electrochemical apparatus of claim 22, wherein said component includes at least one selected from the group consisting of CO and NO.

31. The electrochemical apparatus of claim 22, wherein said electrolyte is an oxygen ion-conducting electrolyte.

32. The electrochemical apparatus of claim 31, wherein said oxygen ion-conducting electrolyte comprises at least one selected from the group consisting of $ZrO_2$, $Bi_2O_3$ and $CeO_2$.

33. The electrochemical apparatus of claim 22, further comprising a reference electrode in contact with said electrolyte.

34. A solid state electrochemical cell for measuring the concentration of CO in a gas mixture, comprising:
a first semiconductor electrode, said first semiconductor electrode comprising a first semiconductor material selected so as to undergo a change in resistivity upon contacting CO, wherein said first semiconductor material includes at least one selected from the group consisting of $TiO_2$, $TYPd_5$, $MoO_3$, $ZnMoO_4$ and $WR_3$;
a second electrode; and
an electrolyte in contact with said first and second electrodes.

35. The electrochemical cell of claim 34, wherein said second electrode comprises a second semiconductor material.

36. The electrochemical cell of claim 35, wherein said second semiconductor material comprises a metal oxide, said metal oxide selected from the group consisting of $SnO_2$, $TiO_2$, $TYPd_5$, $MoO_3$, $ZnMoO_4$ and $WR_3$.

37. The electrochemical cell of claim 36, wherein said first semiconductor material has a voltage response when exposed to CO, said voltage response opposite in slope direction to that of said second semiconductor material, whereby a voltage signal measured across said first and second electrodes is substantially equal to the sum of the absolute values of individual voltage responses of said first and second electrodes.

38. The electrochemical cell of claim 34, further comprising at least one metal layer disposed on at least a potion of said first semiconductor material.

39. The electrochemical cell of claim 34, further comprising a detector for measuring an electrical characteristic generated by said electrochemical cell.

40. The electrochemical cell of claim 34, further comprising a reference electrode in contact with said electrolyte.

41. A method for measuring the concentration of CO in a gas mixture, comprising the steps of:
   exposing said gas mixture to a solid state electrochemical cell, said electrochemical cell formed from:
   (i) a semiconductor electrode, said semiconductor electrode comprising a semiconductor material, said semiconductor material selected so as to undergo a change in resistivity upon contacting CO, wherein said semiconductor material includes at least one selected from the group of materials consisting of $TiO_2$, $TYPd_5$, $MoO_3$, $ZnMoO_4$, $WR_3$,
   (ii) a second electrode, and
   (iii) an electrolyte in contact with said first and second electrodes; and
   measuring an electrical signal generated by said electrochemical cell to determine the concentration of said component.

42. A method for measuring the concentration of a component of a gas mixture comprising the steps of:
   exposing said gas mixture to a solid state electrochemical cell, said solid state electrochemical cell formed from:
   (i) a first semiconductor electrode
   (ii) a second semiconductor electrode, said electrodes comprising first and second semiconductor materials, said materials selected so as to undergo a change in resistivity upon contacting said component, and
   (iii) an electrolyte in contact with said first and second semiconductor electrodes; and,
   measuring an electrical signal generated by said electrochemical cell to determine the concentration of said component.

43. The method of claim 42, wherein said first semiconductor material exhibits a voltage response when exposed to said component, said voltage response opposite in slope direction to that of said second semiconductor material, whereby a voltage signal measured across said electrodes is substantially equal to the sum of the absolute values of individual voltage responses of said electrodes.

44. The method of claim 42, wherein at least one of said semiconductor materials comprises a metal oxide.

45. The method of claim 44, wherein said metal oxides are selected from the group consisting of $SnO_2$, $TiO_2$, $TYPd_5$, $MoO_3$, $ZnMoO_4$ and $WR_3$.

46. The method of claim 42, wherein said component includes CO.

47. A method for operating a combustion engine, comprising the steps of:
   providing an electrochemical cell including:
   (i) a first semiconductor electrode;
   (ii) a second semiconductor electrode, said electrodes comprising first and second semiconductor materials, respectively, said materials selected so as to undergo a change in resistivity upon contacting said pollutant; and
   (iii) an electrolyte in contact with said first and second semiconductor electrodes;
   electrochemically determining the concentration of at least one exhaust pollutant emitted by said combustion engine during operation, and
   adjusting combustion conditions based on concentrations of said exhaust pollutant determined in said determining step.

48. The method of claim 47, wherein said electrochemical cell further comprises at least one metal layer disposed on a portion of at least one of said semiconductor electrodes.

49. The method of claim 47, wherein a plurality of said electrochemical cells are provided for detection of at least two exhaust pollutants.

50. The method of claim 47, wherein a plurality of said electrochemical cells are connected in series.

51. The method of claim 47, wherein at least one of said first and second semiconductor materials undergo a change in resistivity upon contacting CO and comprise at least one selected from $TiO_2$, $TYPd_5$, $MoO_3$, $ZnMoO_4$ and $Wr_3$.

52. A combustion engine comprising:
   at least one cylinder, said cylinder for combusting a fuel mixture therein, said engine emitting a gas mixture comprising a plurality of pollutants;
   an electrochemical emission sensor disposed to receive said emitted gas mixture for determining the concentration of at least one of said plurality of pollutants, wherein said emission sensor comprises an electrochemical cell, said electrochemical cell including a first semiconductor electrode and a second semiconductor electrode, said electrodes comprising first and second semiconductor materials, respectively, said materials selected so as to undergo a change in resisitivity upon contacting said pollutants, and an electrolyte in contact with said first and second semiconductor electrodes, and
   a feedback and control system for receiving pollutant gas concentration data from said emission sensor and for directing adjustment of engine combustion conditions.

53. The combustion engine of claim 52, wherein said electrochemical cell further comprises at least one metal layer disposed on a portion of at least one of said semiconductor electrodes.

54. The combustion engine of claim 52, wherein said emission sensor includes a plurality of said electrochemical cells.

55. The combustion of engine of claim 54, wherein said plurality of electrochemical cells are connected in series.

56. The combustion engine of claim 52, wherein at least one of said first and second semiconductor materials undergo a change in resistivity upon contacting CO and comprise at least one selected from the group consisting of $TiO_2$, $YTPd_5$, $MoO_3$, $ZnMoO_4$ and $WR_3$.

57. The combustion engine of claim 52, wherein said first semiconductor material exhibits a voltage response when exposed to said pollutants, said voltage response opposite in slope direction to that of said second semiconductor material, whereby a voltage signal measured across said electrodes is substantially equal to the sum of the absolute values of individual voltage responses of said electrode.

58. A method of forming a solid state electrochemical cell for measuring the concentration of a component of a gas mixture, comprising the steps of:
   forming a first semiconductor electrode and a second semiconductor electrode, said electrodes comprising first and second semiconductor materials, said materials selected so as to undergo a change in resistivity upon contacting said component, and
   forming an electrolyte, said electrolyte being in contact with said first and second semiconductor electrodes.

59. A method for controlling a chemical process, comprising the steps of:
   providing an electrochemical cell comprising:
   (i) a first semiconductor electrode;
   (ii) a second semiconductor electrode, said electrodes comprising first and second semiconductor materials, respectively, said materials selected so as to undergo a change in resistivity upon contacting gases, and (iii) an electrolyte in contact with said first and second semiconductor electrodes;

electrochemically determining the concentration of at least one gas emitted during operation of said chemical process; and adjusting chemical process conditions based on concentrations of said gas determined in said determining step.

60. The method of claim 59, wherein said chemical process is a combustion process.

61. The method of claim 59, wherein said first semiconductor material exhibits a voltage response when exposed to said gas, said voltage response opposite in slope direction to that of said second semiconductor material, whereby a voltage signal measured across said electrodes is substantially equal to the sum of the absolute values of individual voltage responses of said electrodes.

62. A solid state electrochemical cell for measuring the concentration of NO in a gas mixture, comprising:

a first semiconductor electrode, said first semiconductor electrode comprising $La_2CuO_4$;

a second semiconductor electrode; and an electrolyte in contact with said first and second electrodes.

63. The electrochemical cell of claim 62, wherein said electrochemical cell further comprises at least one metal layer disposed on a portion of at least one of said semiconductor electrodes.

64. The electrochemical cell of claim 62, wherein said electrolyte comprises at least one selected from the group consisting of $ZrO_2$, $Bi_2O_3$ and $CeO_2$.

65. A method for measuring the concentration of NO in a gas mixture, comprising the steps of:

exposing said gas mixture to a solid state electrochemical cell, said electrochemical cell formed from:
  (i) a semiconductor electrode comprising $La_2CuO_4$;
  (ii) a second semiconductor electrode, and
  (iii) an electrolyte in contact with said first and second electrodes; and measuring an electrical signal generated by said electrochemical cell to determine the concentration of NO in said gas mixture.

* * * * *